United States Patent
Schreiber et al.

(10) Patent No.: US 12,193,930 B2
(45) Date of Patent: Jan. 14, 2025

(54) ACCOMMODATIVE INTRAOCULAR LENS

(71) Applicant: Carl Zeiss Meditec AG, Jena (DE)

(72) Inventors: Benjamin Schreiber, Berlin (DE); André Wolfstein, Berlin (DE); Uwe Wolf, Magdala (DE); Jan Buchheister, Jena (DE); Sergio Luque, Vienna (AT)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/119,764

(22) Filed: Mar. 9, 2023

(65) Prior Publication Data

US 2023/0210656 A1 Jul. 6, 2023

Related U.S. Application Data

(63) Continuation of application No. PCT/EP2021/073251, filed on Aug. 23, 2021.

(30) Foreign Application Priority Data

Sep. 9, 2020 (DE) ..................... 10 2020 123 518.6

(51) Int. Cl.
 A61F 2/16 (2006.01)
(52) U.S. Cl.
 CPC .......... *A61F 2/1635* (2013.01); *A61F 2/1648* (2013.01); *A61F 2002/16901* (2015.04)
(58) Field of Classification Search
 None
 See application file for complete search history.

(56) References Cited

U.S. PATENT DOCUMENTS

| | | | |
|---|---|---|---|
| 6,969,403 B2 | 11/2005 | Peng et al. | |
| 2008/0161914 A1* | 7/2008 | Brady | A61F 2/1635 623/6.46 |

(Continued)

FOREIGN PATENT DOCUMENTS

| | | |
|---|---|---|
| DE | 60307816 T2 | 2/2007 |
| DE | 102018212774 B3 | 10/2019 |

OTHER PUBLICATIONS

Office Action issued in German Patent Application No. DE 10 2020 123 518.6 (from which this application claims priority), dated Jun. 21, 2021, and English language machine translation thereof.

(Continued)

*Primary Examiner* — Leslie A Lopez
(74) *Attorney, Agent, or Firm* — Ewers IP Law PLLC; Falk Ewers

(57) ABSTRACT

An accommodative intraocular lens includes a first lens part, a haptic, and a flexible membrane. The flexible membrane is arranged adjacent to a distal optical body surface, delimits a cavity together with the distal optical body surface and is transparent to light. A second lens part has a hollow cylinder coupled releasably to the first lens part, as a result of which the intraocular lens can be brought into a coupling state in which the second lens part is arranged on a distal side of the first lens part and the hollow cylinder is configured to deform the membrane by a longitudinal displacement of the hollow cylinder parallel to the optical axis. The hollow cylinder has on its exterior an outer face and a bearing face arranged adjacent to a proximal end of the outer face and encloses, with the outer face, an angle of less than 180°.

3 Claims, 5 Drawing Sheets

(56) References Cited

U.S. PATENT DOCUMENTS

| | | | | |
|---|---|---|---|---|
| 2012/0296424 | A1* | 11/2012 | Betser | A61F 2/1629 |
| | | | | 623/6.13 |
| 2014/0180404 | A1* | 6/2014 | Tran | A61F 2/1648 |
| | | | | 623/6.13 |
| 2014/0277434 | A1* | 9/2014 | Weeber | A61F 2/161 |
| | | | | 623/6.18 |
| 2014/0309734 | A1* | 10/2014 | Sohn | A61F 2/1648 |
| | | | | 623/6.34 |
| 2017/0224475 | A1 | 8/2017 | Weeber et al. | |
| 2018/0185139 | A1* | 7/2018 | Sohn | A61F 2/1629 |
| 2019/0374334 | A1* | 12/2019 | Brady | A61F 2/1645 |
| 2021/0145569 | A1 | 5/2021 | Sergio et al. | |

OTHER PUBLICATIONS

International Search Report dated Nov. 29, 2021, of international application PCT/EP2021/073251 on which this application is based, and English language machine translation thereof.

International Preliminary Report on Patentability issued in International Patent Application No. PCT/EP2021/073251 (on which this application is based), dated Mar. 9, 2023, and English language translation thereof.

* cited by examiner

ACCOMMODATIVE INTRAOCULAR LENS

CROSS REFERENCE TO RELATED APPLICATIONS

This application is a continuation application of international patent application PCT/EP2021/073251, filed Aug. 23, 2021, designating the United States and claiming priority to German application 10 2020 123 518.6, filed Sep. 9, 2020, and the entire content of both applications is incorporated herein by reference.

TECHNICAL FIELD

The disclosure relates to an accommodative intraocular lens.

BACKGROUND

A natural lens of the eye allows objects in the distance and in the vicinity to be seen clearly. This is facilitated by virtue of the lens of the eye being able to alter its form and hence the refractive power. The lens of the eye is contained in a capsular bag which is suspended from zonular fibers which, in turn, are connected to ciliary muscle. When the ciliary muscle relaxes, the zonular fibers tighten, stretching the capsular bag. In the case of a soft lens of the eye, the changing shape of the capsular bag causes the former to also change its shape. As the capsular bag is stretched, the lens of the eye becomes increasingly flattened. This changes the refractive power of the lens of the eye. A flattened lens of the eye leads to a lower refractive power, and so sharp distance vision is possible. This process is reversible, so that when the ciliary muscle is tense, the zonular fibers slacken, and the capsular bag is less stretched. Hence, the lens of the eye assumes a shape that is more curved, and so a higher refraction is achieved. This makes it possible to see objects in the vicinity clearly. This variation in the plane of focus is called accommodation.

It is normal for the lens of the eye to lose elasticity with age. The lens of the eye is then less able to change its shape in response to a contraction of the ciliary muscle. This makes it increasingly difficult to focus on close objects. This condition is known as presbyopia. By wearing spectacles or a contact lens, it is possible to compensate the missing refractive power. With increasing age, however, the lens of the eye becomes increasingly inelastic to hard and can also become cloudy. In medicine, such a condition of the lens of the eye is called a cataract. A spectacle lens cannot compensate for the consequences of clouding of the lens of the eye, and so it has become common to remove the clouded lens of the eye by surgery. To this end, for example, a needle vibrating with ultrasound is inserted into the eye and the hard and cloudy lens of the eye is comminuted into small particles. This process is known as phacoemulsification. Following such phacoemulsification, the particles are aspirated until the capsular bag has been freed from the natural lens of the eye. To enable good vision again, an artificial lens of the eye is subsequently implanted in the capsular bag. This artificial lens of the eye is called an intraocular lens.

The artificial lens of the eye is usually a lens with a single focal point (monofocal), and so a patient needs spectacles or a contact lens for clear distance and near vision after an artificial lens of the eye has been implanted. However, there are also thoughts of designing the artificial lens of the eye in such a way that accommodation with a changing plane of focus is possible. Such an artificial lens of the eye is also referred to as an accommodative intraocular lens. Tensing or relaxing a ciliary muscle should make it possible to change the shape of the intraocular lens, and hence its refractive power. What is problematic here, however, is that it is difficult to transmit a force from the capsular bag to the intraocular lens in order to change the shape of the intraocular lens.

SUMMARY

It is therefore an object of the disclosure to develop an accommodative intraocular lens with which a force can be transmitted well from a capsular bag to the intraocular lens.

The accommodative intraocular lens according to an aspect of the disclosure for insertion into the capsular bag of an eye includes a first lens part including an optic body which is transparent to light, and which has an optical axis, a distal optic body surface, and a proximal optic body surface, a haptic firmly connected to the optic body, a flexible membrane which is firmly connected to the haptic and/or the optic body and which is arranged adjacent to the distal optic body surface, delimits a cavity together with the distal optic body surface, and is transparent to the light, and a second lens part which has a hollow cylinder with a distal end and a proximal end and which can be detachably coupled to the first lens part, whereby the intraocular lens is able to be brought into a coupling state in which the second lens part is arranged on a distal side of the first lens part and the hollow cylinder is configured to deform the membrane by way of a longitudinal displacement of the hollow cylinder parallel to the optical axis, with the hollow cylinder having on its outer side an outer surface, which is an outer end of the hollow cylinder in the radial direction with respect to the axis of the hollow cylinder, and having a bearing surface which is arranged adjacent to a proximal end of the outer surface and includes an angle of less than 180° with the outer surface.

In order to insert the intraocular lens into the capsular bag of an eye, it is conceivable to cut out a part of the capsular bag that is as circular as possible. This creates a cut edge, the cut edge also being called rhexis. The first lens part is inserted into the capsular bag first, followed by the second lens part. The haptic comes into engagement with the capsular bag when the first lens part is inserted, as a result of which the optic body is arranged centrally in the capsular bag. The second lens part is subsequently arranged in the capsular bag in such a way that the intraocular lens reaches the coupling state. The distal end of the hollow cylinder can subsequently be introduced into the part of the capsular bag that has been cut out, as a result of which the capsular bag contacts the bearing surface. This creates a good mechanical coupling between the capsular bag and the hollow cylinder. As a result, a force can be effectively transmitted from the capsular bag to the hollow cylinder. The force can subsequently be transmitted from the hollow cylinder to the membrane, which deforms as a result and thus experiences a change in its radius of curvature. The membrane changes its refraction by virtue of the membrane changing its radius of curvature, with the result that an accommodation of the eye to distant or near objects is achievable. When the hollow cylinder moves perpendicularly to the optical axis, the rhexis butts against the outer surface, with the result that the hollow cylinder is secured against slipping.

It is typical for the axis of the hollow cylinder to be substantially parallel to the optical axis in the coupling state. The axis of the hollow cylinder and the optical axis particularly typically coincide in the coupling state.

It is typical for the bearing surface to be arranged immediately adjacent to the proximal end of the outer surface.

It is typical for the outer surface to have the shape of the surface of a cylinder. In this case, it is particularly typical for the axis of the cylinder to coincide with the axis of the hollow cylinder.

The bearing surface typically has the shape of an annulus. The normal of the annulus is particularly typically parallel to the axis of the cylinder.

The angle between the outer surface and the bearing surface is typically 80° to 135°. Particularly typically, the angle between the outer surface and the bearing surface is 80° to 100° or 90°.

It is typical for the second lens part to have a groove surface which faces the bearing surface and is arranged immediately adjacent to a distal end of the outer surface, with the outer surface, the bearing surface, and the groove surface delimiting a groove. In this case, it is particularly typical for the groove to be circumferential in the circumferential direction with respect to the optical axis and in particular extend along the entire circumference of the hollow cylinder.

The second lens part typically has a clamping ring which is configured to be arranged adjacent to the outer surface and the bearing surface and is thus configured to clamp the capsular bag. In the process, it is conceivable for the capsular bag to be clamped between the bearing surface and the clamping ring. By virtue of the capsular bag being clamped, the hollow cylinder is coupled particularly firmly to the capsular bag. As a result, a force can be particularly effectively transmitted from the capsular bag to the hollow cylinder. Moreover, the hollow cylinder is particularly firmly secured against slipping. Moreover, it is conceivable that the clamping ring contacts the outer surface. It is particularly typical for the clamping ring to be introduced into the groove.

The clamping ring is typically a split ring. The split ring can be advantageously easily arranged on the outer surface and the bearing surface. It is typical for the split ring to have a first longitudinal end and a second longitudinal end, which delimit a gap in the split ring, the split ring having a first cutout in the region of the first longitudinal end and a second cutout in the region of the second longitudinal end. By way of example, a respective rod can be introduced into each of the two cutouts. The split ring can be spread apart by virtue of moving the two rods apart, and this allows easy placement of the split ring on the outer surface and the bearing surface. It is particularly typical for the split ring to have a first thickening at its first longitudinal end and a second thickening at its second longitudinal end, with the first cutout being arranged in the said first thickening and the second cutout being arranged in the said second thickening. As a result, more space is available for the cutouts than in the case where the thickenings are not provided.

It is typical that the outer surface is formed by a thread which extends up to the distal end. In this case, it is conceivable for a screw nut to be screwed onto the thread after the hollow cylinder has been inserted into the capsular bag, and for the capsular bag to be clamped between the bearing surface and the screw nut.

It is typical for the second lens part to include a screw nut which has a groove surface and which is screwed onto the thread, whereby the groove surface faces the outer surface, is arranged immediately adjacent to the outer surface, and delimits the groove together with the bearing surface and the outer surface. By screwing the screw nut in the direction of the proximal end of the hollow cylinder, the groove can be narrowed, and the capsular bag can be coupled particularly firmly to the hollow cylinder. As a result, the hollow cylinder is also particularly firmly secured against slipping. It is particularly typical for the screw nut to be formed by a ring which has a screw nut cutout. A rod can be inserted into the screw nut cutout and the screw nut can be rotated with the rod.

It is typical for the second lens part to have an open state and a closed state, in which the second lens part has a groove surface which faces the bearing surface, which is arranged immediately adjacent to a distal end of the outer surface, and which delimits a groove together with the outer surface and the bearing surface, with the groove surface not being present and the groove not being formed in the open state. As a result, the distal end of the hollow cylinder can be easily inserted into the cut-out part of the capsular bag when the second lens part is in the open state. The hollow cylinder can subsequently be attached particularly firmly to the capsular bag by virtue of the second lens part being brought into the closed state.

The second lens part particularly typically includes a shape memory material with a transition temperature, with the second lens part being configured to be brought from the open state to the closed state when the transition temperature is exceeded. By way of example, the transition temperature can be a glass transition temperature or a melting temperature, and the hollow cylinder can be under mechanical prestress below the transition temperature. As a result of the transition temperature being exceeded, the second lens part loses at least some of the mechanical prestress and thus reaches the closed state. The transition temperature can be chosen to be above body temperature, for example higher than 42° C. The second lens part can be heated to temperatures above the transition temperature by irradiation with electromagnetic radiation, for example with a laser.

The first lens part typically has a plurality of bending elements which are attached to the membrane outside the cavity, and which contact a proximal end of the hollow cylinder in the coupling state.

It is typical for the cavity to be filled with a gas, an oil, in particular a silicone oil, or a gel, in particular a silicone gel. This is advantageous since gas has a different refractive index to an optic body formed from an acrylic polymer material or a membrane. The refractive index of an acrylic polymer is at approximately 1.47 to 1.55 and the refractive index of a gas such as air is at approximately 1.00003, with these values applying at the wavelength of 589 nm of the sodium D-line. Consequently, a refractive index difference of approximately 0.5 can be achieved by using a gas in the cavity. If the height of the cavity alters due to a displacement of the hollow cylinder and the membrane relative to the optic body so that there is a change in the gas volume present between the membrane and the anterior optic body surface, then there is a change in the refractive power of the entire intraocular lens as a consequence. A relatively large change in refraction can already be achieved by a small accommodation and hence displacement of hollow cylinder and membrane relative to the optic body and thus change in the radius of curvature of the membrane. A different refractive index like for the optic body and the membrane can also be chosen for the oil and the gel.

BRIEF DESCRIPTION OF THE DRAWINGS

The disclosure will now be described with reference to the drawings wherein.

DESCRIPTION OF EXEMPLARY EMBODIMENTS

Figure 5:
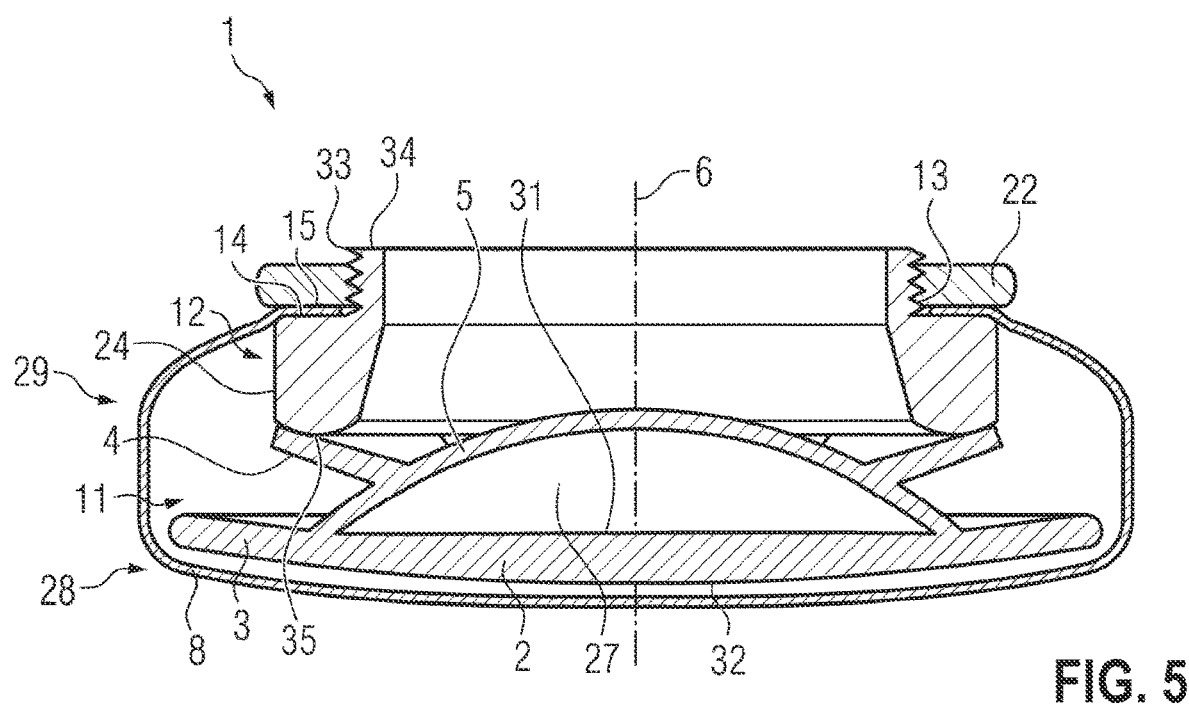
FIG. 5 shows a section through the intraocular lens according to a third exemplary embodiment of the disclosure.
Figure 6:
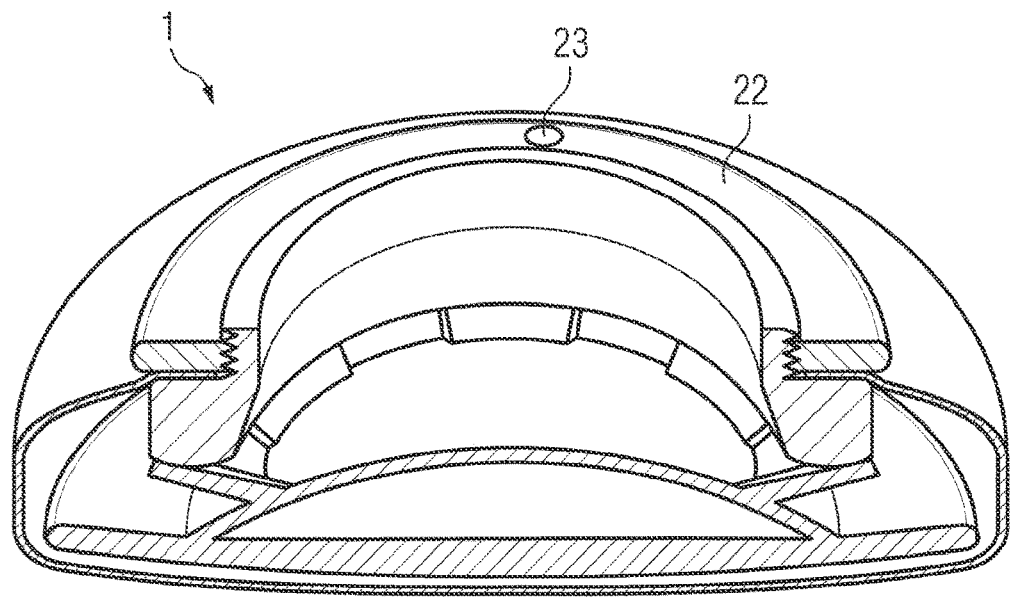
FIG. 6 shows a different perspective of the section shown in FIG. 5.
Figure 7:
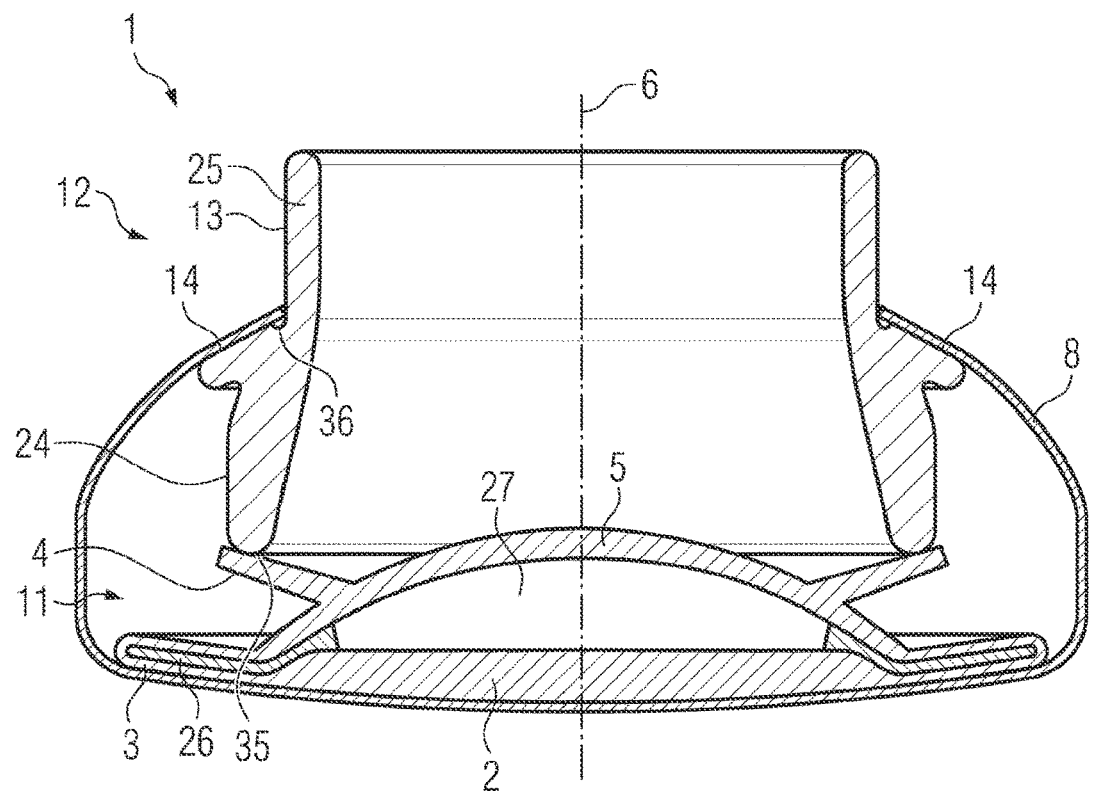
FIG. 7 shows a section of the intraocular lens in an open state according to a fourth exemplary embodiment of the disclosure.
Figure 8:
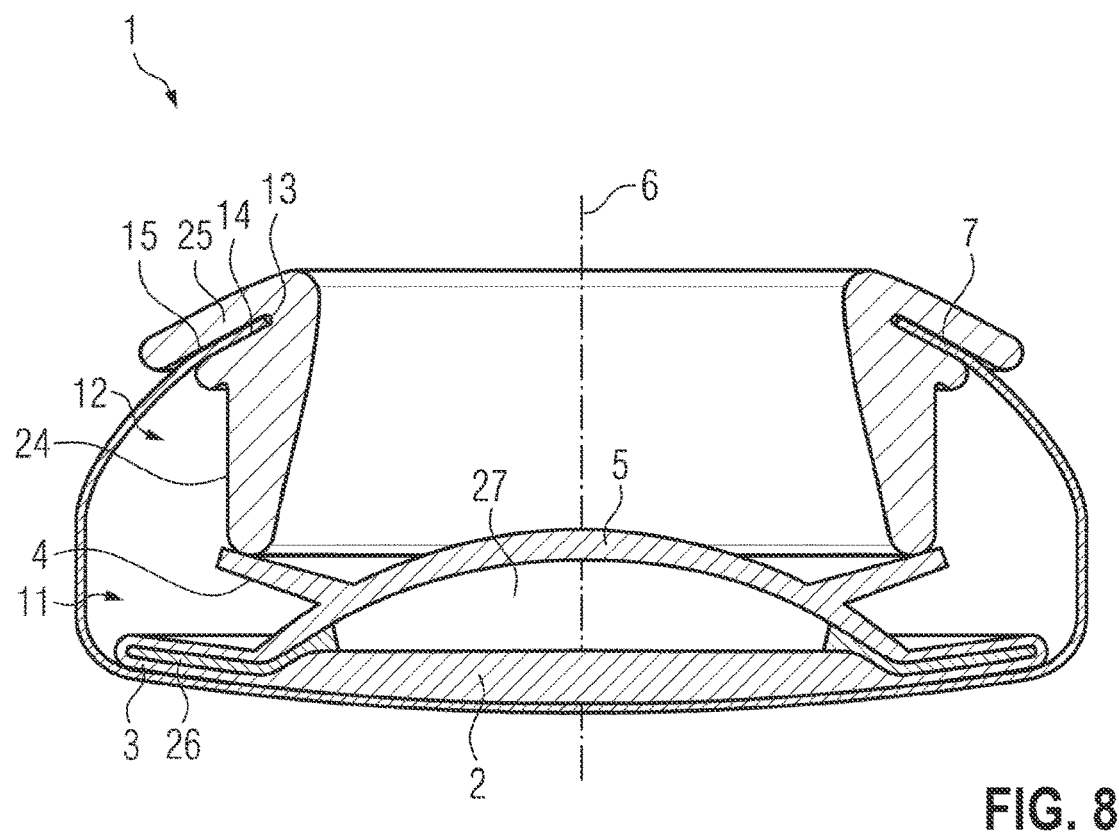
FIG. 8 shows a section of the intraocular lens in a closed state according to the fourth exemplary embodiment of the disclosure.
Figure 9:
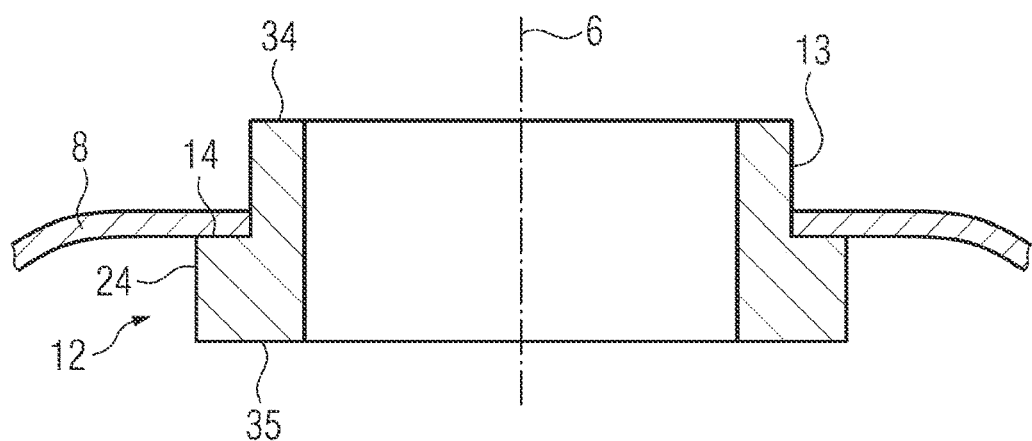
FIG. 9 shows a section through a hollow cylinder of the intraocular lens according to a fifth exemplary embodiment of the disclosure.

As shown in FIGS. 1 to 9, an accommodative intraocular lens 1 includes the following for the insertion thereof into the capsular bag 8 of an eye: a first lens part 11 including an optic body 2 which is transparent to light, and which has an optical axis 6, a distal optic body surface 31, and a proximal optic body surface 32, a haptic 3 firmly connected to the optic body 2, a flexible membrane 5 which is firmly connected to the haptic 3 and/or the optic body 2 and which is arranged adjacent to the distal optic body surface 31, delimits a cavity 27 together with the distal optic body surface 31, and is transparent to the light, and a second lens part 12 which has a hollow cylinder 24 with a distal end 34 and a proximal end 35 and which can be detachably coupled to the first lens part 11, whereby the intraocular lens 1 is able to be brought into a coupling state in which the second lens part 12 is arranged on a distal side 29 of the first lens part 11 and the hollow cylinder 24 is configured to deform the membrane 5 by way of a longitudinal displacement of the hollow cylinder 24 parallel to the optical axis 6, with the hollow cylinder 24 having on its outer side an outer surface 13, which is an outer end of the hollow cylinder 24 in the radial direction with respect to the axis of the hollow cylinder 24, and having a bearing surface 14 which is arranged adjacent to a proximal end of the outer surface 13 and includes an angle of less than 180° with the outer surface 13. It is conceivable for the axis of the hollow cylinder 24 to be substantially parallel to the optical axis 6 in the coupling state, as is also apparent from FIGS. 1 to 9. The cavity 27 can be hermetically sealed. Moreover, the cavity 27 can be filled with a gas, an oil, in particular a silicone oil, or a gel, in particular a silicone gel. FIGS. 7 and 8 show that the cavity 27 can have a reservoir 26 which is arranged in the haptic 3. As the membrane deforms, the gas, the oil, or the gel can flow out of the reservoir 26 and into the reservoir 26.

The bearing surface 14 can be arranged immediately adjacent to the proximal end of the outer surface 13. This is shown by way of example in FIGS. 1 to 3, 5, 6, 8, and 9.

By way of example, the angle can have a value of 80° to 135°, as is the case in the exemplary embodiments shown in FIGS. 1 to 3 and 5 to 9, for example. By way of example, the angle can also be between 80° and 100°, as is the case in the embodiments shown in FIGS. 1 to 3, 5, 6, 8, and 9, for example. In another example, the angle can be 90°, as is the case in the exemplary embodiments shown in FIGS. 1 to 3, 5, 6, and 9, for example.

It is conceivable that the outer surface 13 and the bearing surface 14 extend along the entire circumference of the hollow cylinder 24. The outer surface 13 can have the shape of the surface of a cylinder, with the axis of the cylinder being able to coincide with the axis of the hollow cylinder 24. With regards to the bearing surface 14, it is conceivable that the latter has the shape of an annulus. The normal of the annulus can be parallel to the axis of the cylinder.

FIGS. 1 to 3 and 5 to 8 show that the first lens part 11 can have a plurality of bending elements 4 which are attached to the membrane 5 outside the cavity 27 and which contact the proximal end 35 of the hollow cylinder 24 in the coupling state. In the circumferential direction with respect to the optical axis 6, the bending elements 4 can be provided on the membrane 5 as radially outwardly directed bending elements 4 in the form of a bending beam fixed to the membrane 5 on one side. The bending elements 4 can be arranged in relation to one another at the same horizontal angle or in the azimuth. In the coupling state, the proximal end 35 of the hollow cylinder 24 can be seated on the bending elements 4.

FIGS. 1 to 3 and 5 to 9 show a state of the intraocular lens 1 in which the intraocular lens 1 is in the coupling state and in which the intraocular lens 1 is inserted in the capsular bag 8. A substantially circular part was cut out of the capsular bag 8, with the result that a substantially circular cut edge remained in the eye. The distal end 34 of the hollow cylinder 24 is arranged in the cut-out part of the capsular bag 8.

FIGS. 1 to 3 and 5 to 8 show that the second lens part 12 can have a groove surface 15 which faces the bearing surface 14 and is arranged immediately adjacent to a distal end of the outer surface 13, with the outer surface 13, the bearing surface 14, and the groove surface 15 delimiting a groove 7. It is conceivable that the groove 7 is circumferential in the circumferential direction with respect to the optical axis 6. Moreover, it is conceivable that the groove 7 extends along the entire circumference of the hollow cylinder 24. FIGS. 1 to 3, 5 and 6 show that the bearing surface 14 and the groove surface 15 can be arranged parallel to each other. The groove 7 can have a width of 200 μm to 400 μm, in particular 250 μm to 350 μm, for example in the direction of the axis of the hollow cylinder 24.

Figure 1:
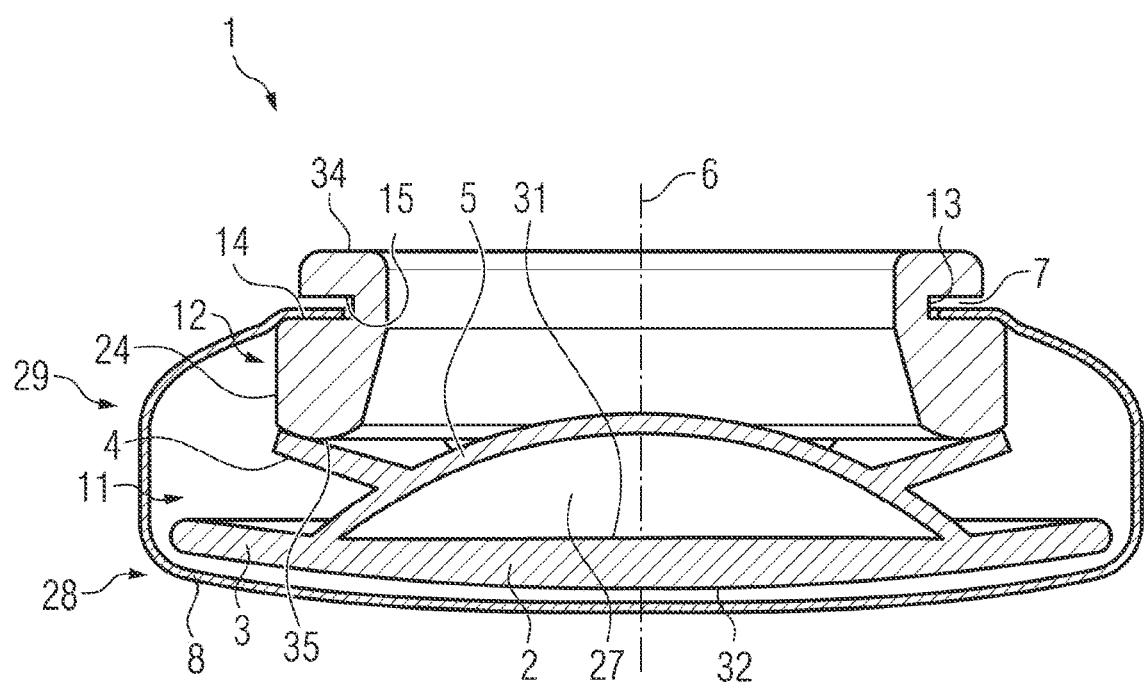
FIG. 1 shows a section through an intraocular lens according to a first exemplary embodiment of the disclosure.
Figure 2:
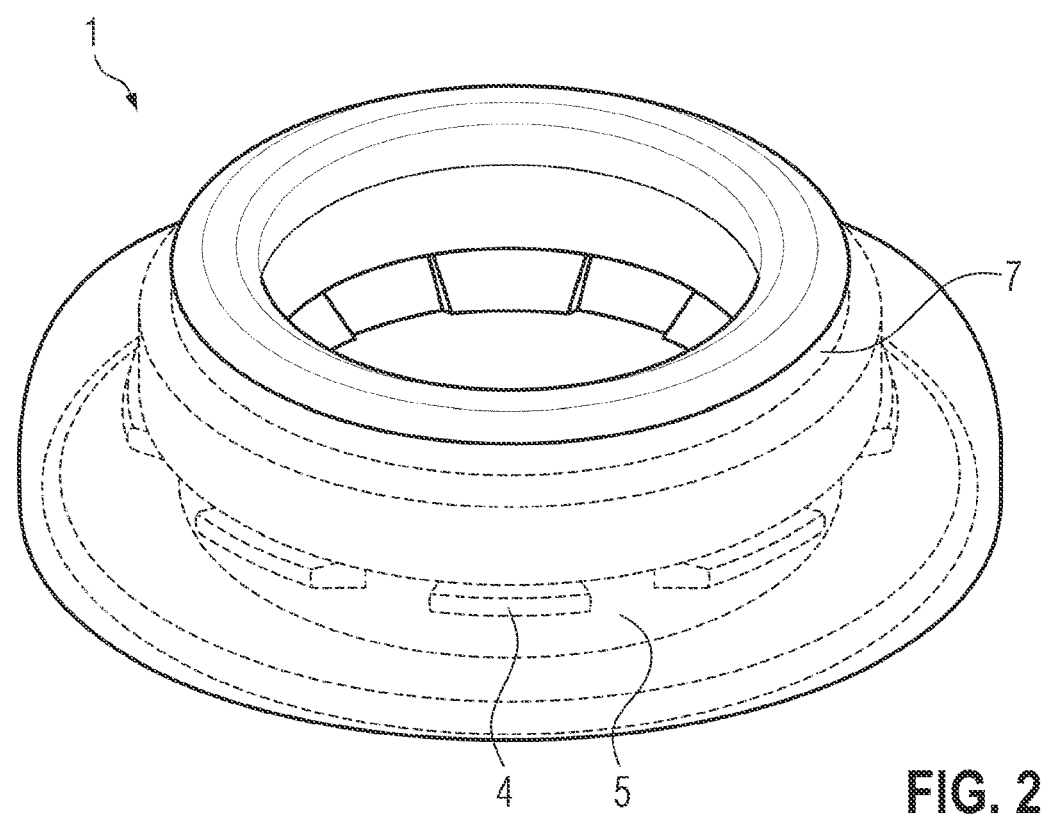
FIG. 2 shows a perspective view of the first exemplary embodiment of the disclosure.

According to a first exemplary embodiment of the intraocular lens 1, as shown in FIGS. 1 and 2, the capsular bag 8 can be introduced only into the groove 7, without another component being introduced into the groove 7. In this case, the first lens part 11 has no further component in addition to the hollow cylinder 24.

Figure 3:
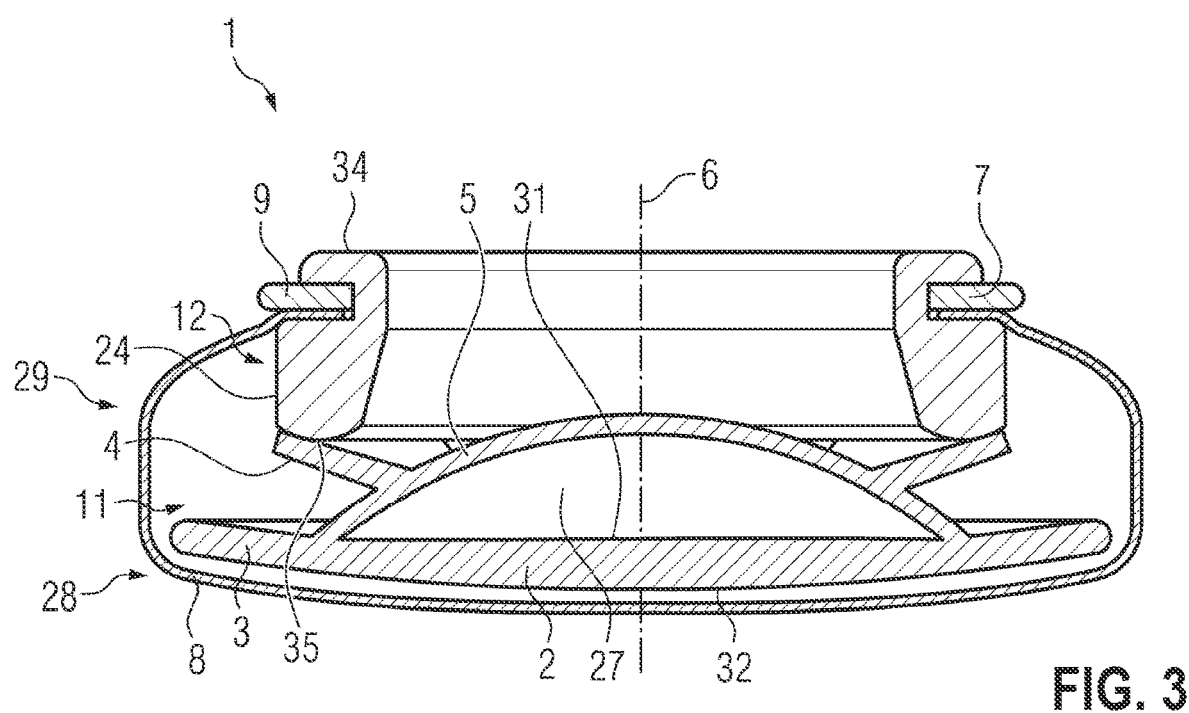
FIG. 3 shows a section through the intraocular lens according to a second exemplary embodiment of the disclosure.
Figure 4:
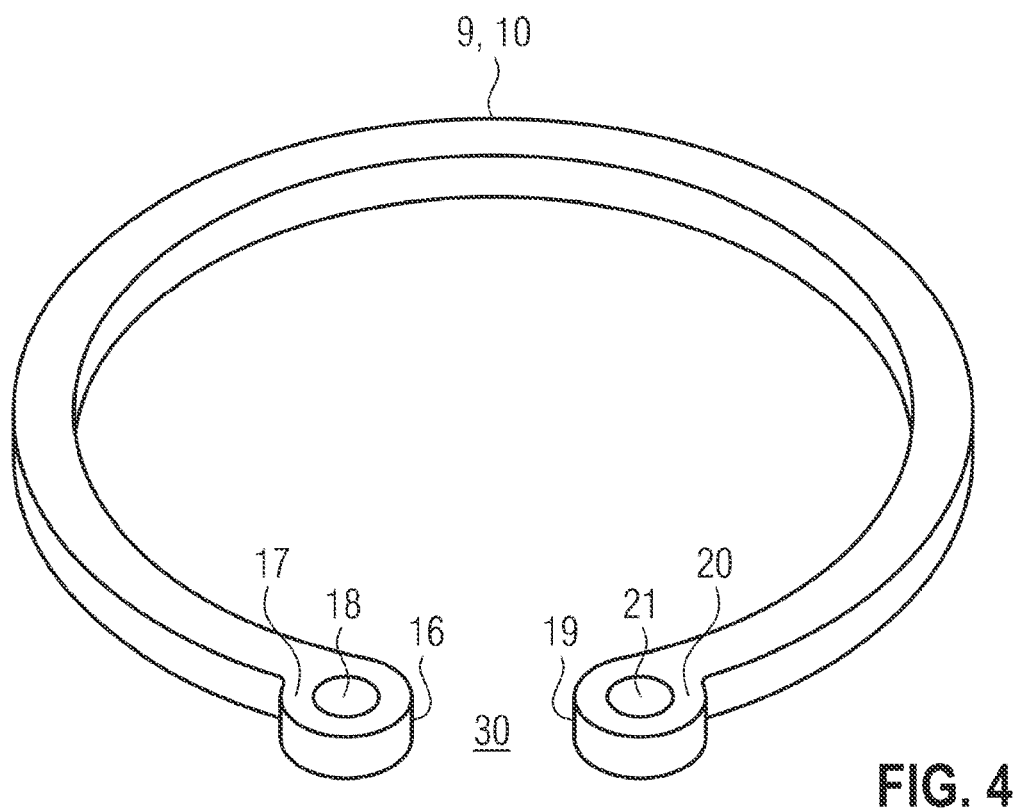
FIG. 4 shows a perspective view of a component of the second exemplary embodiment of the disclosure.

According to a second exemplary embodiment of the intraocular lens 1 shown in FIGS. 3 and 4, the second lens part 12 can include a clamping ring 9 which is configured to be inserted into the groove 7 and is therefore configured to clamp the capsular bag 8 in the groove 7.

According to a first variant of the second exemplary embodiment, the clamping ring 9 can be a split ring 10, as shown by way of example in FIG. 4. The split ring 9 has a first longitudinal end 16 and a second longitudinal end 19, which delimit a gap 30 of the split ring 10. FIG. 4 shows that the split ring 10 can have a first cutout 18 in the region of the first longitudinal end 16 and a second cutout 21 in the region of the second longitudinal end 19. In this case, the first cutout 18 and the second cutout 21 can be introduced into a side that faces away from the first lens part 11 when the split ring 10 is arranged in the groove 7 and the intraocular lens 1 is in the coupling state. Moreover, the normal of the side can be parallel to the axis of the hollow cylinder 24. The first cutout 18 and the second cutout 21 can each be formed as a through hole. It is also apparent from FIG. 4 that the split ring 10 has a first thickening 17 at its first longitudinal end 16 and a second thickening 20 at its second longitudinal end 19, with the first cutout 18 being arranged in the said first thickening and the second cutout 21 being arranged in the said second thickening.

According to a second variant of the second exemplary embodiment, the clamping ring 9 can be designed without a gap, that is to say the clamping ring 9 extends through an angle of 360°.

FIGS. 5 and 6 show a third exemplary embodiment of the intraocular lens 1. Here, the outer surface 13 is formed by a thread 33 which extends up to the distal end 34. The second lens part 12 can have a screw nut 22 which is screwed onto the thread 33, as a result of which the groove 7 is delimited in the direction of the optical axis 6 and at its distal end by the screw nut 22. The underside of the screw nut 22 thus forms the groove surface 15. By screwing the screw nut 22 in the direction of the bearing surface 14, the extent of the groove is shortened in the direction of the axis of the hollow cylinder 24 and a part of the capsular bag 8 can be fixed in its position by the bearing surface 14 and the groove surface 15 in form-fitting and/or force-fitting fashion. FIG. 6 shows that the screw nut 22 can be formed by a ring which has a screw nut cutout 23. In this case, the screw nut cutout 23 can be introduced into a side that faces away from the first lens part 11 when the screw nut 22 is arranged in the groove 7 and the intraocular lens 1 is in the coupling state. Moreover, the normal of the side can be parallel to the axis of the hollow cylinder 24. The screw nut cutout 23 may be formed as a through hole.

FIGS. 7 and 8 show a fourth exemplary embodiment for the intraocular lens 1, wherein the second lens part 12 has an open state and a closed state, in which the second lens part 12 has a groove surface 15 which faces the bearing surface 14, which is arranged immediately adjacent to a distal end of the outer surface 13, and which delimits a groove 7 together with the outer surface 13 and the bearing surface 14, with the groove surface 15 not being present and the groove 7 not being formed in the open state. To this end, the hollow cylinder 24 can have a collar 25 which protrudes from the remaining hollow cylinder 24 and forms the groove surface 15 on its outside. As viewed from the axis of the hollow cylinder 24, the collar 25 can extend along an angle of 360°. The bearing surface 14 can be inclined in a direction from radially inward to radially outward in a direction towards a proximal end 35 of the hollow cylinder 24.

It is conceivable that, as shown in FIG. 7, the hollow cylinder 24 in the fourth exemplary embodiment has a groove 36 in the open state, which groove separates the outer surface 13 and the bearing surface 14 from one another so that the outer surface 13 and the bearing surface 14 are not directly adjacent to one another. In the closed state, it is conceivable that the groove 36 becomes the outer surface 13 and that the outer surface 13 becomes the groove surface 15, as illustrated in FIG. 8.

In the fourth exemplary embodiment, it is conceivable that the second lens part 12 includes a shape memory material with a transition temperature, with the second lens part 12 being configured to be brought from the open state to the closed state when the transition temperature is exceeded. By way of example, the transition temperature can be higher than 42° C. The shape memory material can be heated to a temperature above the transition temperature, for example by irradiation with laser radiation. Moreover, it is conceivable that a glass transition or a melting of the shape memory material occurs at the transition temperature. Below the transition temperature, the shape memory material can be under a mechanical prestress, at least some of which is lost when the transition temperature is exceeded.

As an alternative to providing the groove 7, it is conceivable that, in the radial direction with respect to the axis of the hollow cylinder, only the outer surface 13 and the bearing surface 14 are provided on the outside of the hollow cylinder 24 and on the distal end 34 of the hollow cylinder 24. This is shown, for example, in FIG. 9 for a fifth exemplary embodiment of the intraocular lens 1. In the fifth exemplary embodiment, it is conceivable for the second lens part 12 to have the clamping ring 9.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Intraocular lens
2 Optic body
3 Haptic
4 Bending element
5 Membrane
6 Optical axis
7 Groove
8 Capsular bag
9 Clamping ring
10 Split ring
11 First lens part
12 Second lens part
13 Outer surface
14 Bearing surface
15 Groove surface
16 First longitudinal end
17 First thickening
18 First cutout
19 Second longitudinal end
20 Second thickening
21 Second cutout
22 Screw nut
23 Screw nut cutout
24 Hollow cylinder
25 Collar
26 Reservoir
27 Cavity
28 Proximal side of the first lens part
29 Distal side of the first lens part
30 Gap
31 Distal optic body surface
32 Proximal optic body surface
33 Thread
34 Distal end of the hollow cylinder
35 Proximal end of the hollow cylinder
36 Groove

What is claimed is:
1. An accommodative intraocular lens for insertion into a capsular bag of an eye, the intraocular lens comprising:
   a first lens part comprising:

an optic body which is transparent to light, and which has an optical axis, a distal optic body surface, and a proximal optic body surface;

a haptic firmly connected to the optic body;

a flexible membrane which is firmly connected to the haptic and/or the optic body and which is arranged adjacent to the distal optic body surface, wherein the membrane together with the distal optic body surface delimits a cavity, and wherein the membrane is transparent to the light; and a second lens part which has a hollow cylinder, wherein the hollow cylinder has a distal end and a proximal end, and wherein the second lens part can be detachably coupled to the first lens part, wherein the intraocular lens is configured to be brought into a coupling state in which the second lens part is arranged on a distal side of the first lens part and the hollow cylinder is configured to deform the membrane by way of a longitudinal displacement of the hollow cylinder parallel to the optical axis, wherein the first lens part has a plurality of bending elements which are attached to the membrane outside the cavity and which contact the proximal end of the hollow cylinder in the coupling state, wherein the hollow cylinder has on its outer side an outer surface, which is an outer end of the hollow cylinder in a radial direction with respect to an axis of the hollow cylinder, wherein the hollow cylinder further has a bearing surface which is arranged adjacent to a proximal end of the outer surface, which includes an angle of less than 180° with the outer surface, and which is configured to be contacted by the capsular bag, wherein the second lens part has a clamping ring which is configured to be arranged adjacent to the outer surface and the bearing surface and which is thereby configured to clamp the capsular bag, and wherein the clamping ring is a split ring.

2. The intraocular lens as claimed in claim 1, wherein the axis of the hollow cylinder is substantially parallel to the optical axis in the coupling state.

3. The intraocular lens as claimed in claim 1, wherein the second lens part has a groove surface which faces the bearing surface and which is arranged immediately adjacent to a distal end of the outer surface, and wherein the outer surface, the bearing surface, and the groove surface form a groove.

\* \* \* \* \*